United States Patent [19]

Albarda

[11] 4,314,564

[45] Feb. 9, 1982

[54] METHOD AND APPARATUS FOR DETERMINING ALCOHOL CONCENTRATION IN THE BLOOD

[75] Inventor: Scato Albarda, Gross Schenkenberg, Fed. Rep. of Germany

[73] Assignee: Drägerwerk Aktiengesellschaft, Fed. Rep. of Germany

[21] Appl. No.: 112,231

[22] Filed: Jan. 15, 1980

[30] Foreign Application Priority Data

Feb. 22, 1979 [DE] Fed. Rep. of Germany ....... 2906790

[51] Int. Cl.³ .............................................. A61B 5/00
[52] U.S. Cl. ....................................... 128/719; 73/23; 73/29; 73/19-27;29;421.5 R
[58] Field of Search ......... 128/719; 23/232 R, 232 C, 23/232 E, 907; 340/573, 576; 422/84-85

[56] References Cited

U.S. PATENT DOCUMENTS

| | | | |
|---|---|---|---|
| 3,830,630 | 8/1974 | Kiefer et al. ........................ | 128/719 |
| 3,831,707 | 8/1974 | Takeuchi ............................. | 128/719 |
| 4,067,320 | 1/1978 | Olsson et al. ....................... | 128/719 |
| 4,090,078 | 5/1978 | Heim .................................. | 422/84 X |
| 4,140,106 | 2/1979 | Kirmaier ............................. | 128/719 |

*Primary Examiner*—Robert W. Michell
*Assistant Examiner*—Francis J. Jaworski
*Attorney, Agent, or Firm*—McGlew and Tuttle

[57] ABSTRACT

A method and apparatus for determining the alcohol concentration in the blood of a person by testing the person's breath, including, maintaining at least a minimum flow rate for the person's breath to form a test sample of the breath, measuring the alcohol amount in the test sample, measuring the increase in humidity in the test sample over ambient humidity and finding the ratio between the alcohol amount and the increase in humidity. This ratio is proportional to the actual alcohol concentration in the person's blood and cannot be disquised by a person wishing to falsify the results of the test.

13 Claims, 1 Drawing Figure

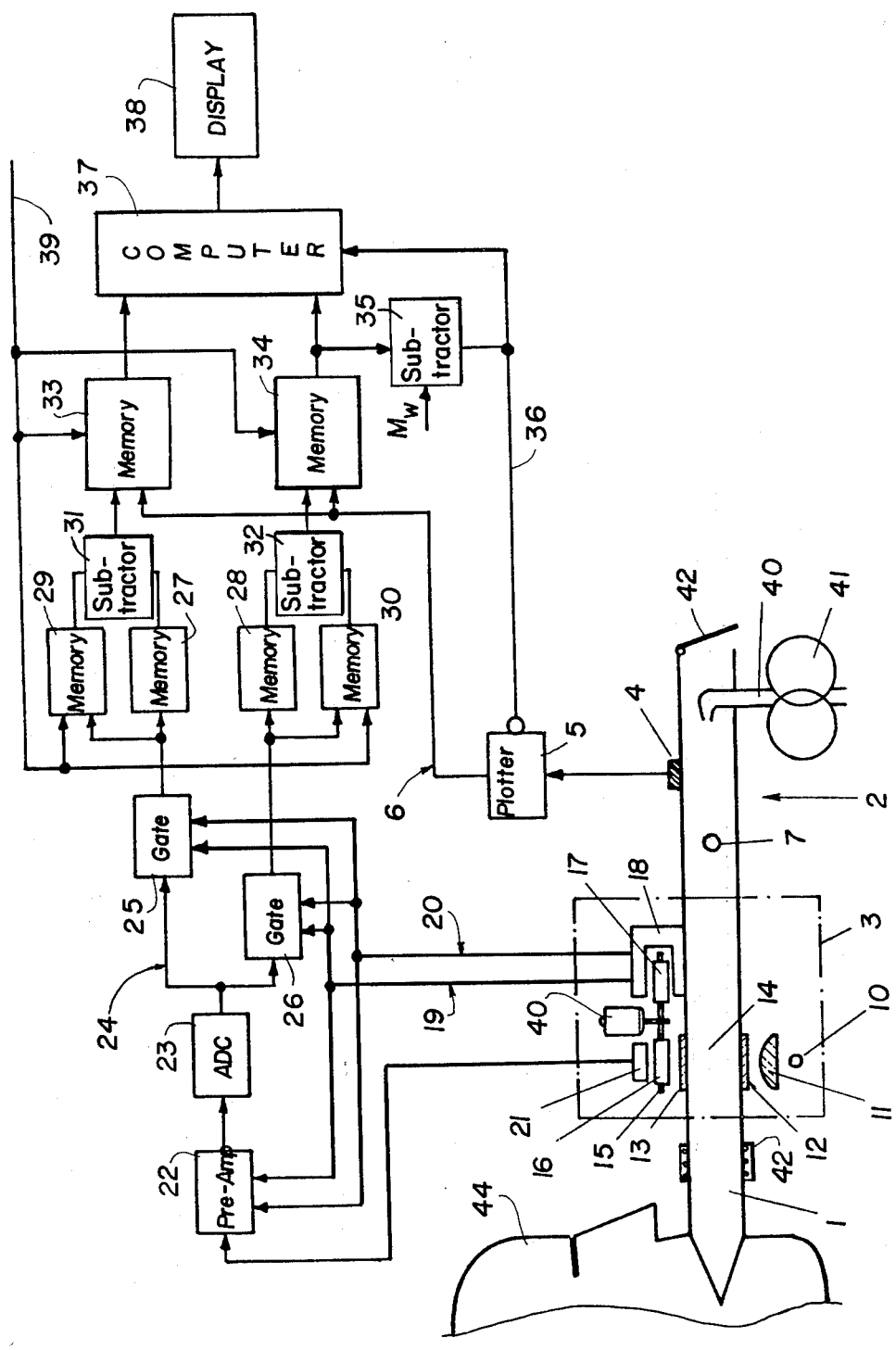

METHOD AND APPARATUS FOR DETERMINING ALCOHOL CONCENTRATION IN THE BLOOD

FIELD AND BACKGROUND OF THE INVENTION

The present invention relates to breath analyzers in general and, in particular, to a new and useful method and apparatus for determining the alcohol concentration in the blood of a person to be tested by measuring the alcohol and humidity concentration in the person's breathing air.

The invention is based on the finding that there is a close relationship between the concentration of alcohol and humidity in air exhaled by a person. When a person to be tested tries to effect an exchange of air in his oral cavity and upper air passages by means of flat breathing to disguise the amount of alcohol which may be on his breath, this hardly affects the measuring result, since the ratio of alcohol to humidity is practically not influenced. When liquid evaporates in the oral pharyngeal space, the alcohol and the water are absorbed into the breathing air in a similar close ratio as in the lungs.

A known arrangement for determining alcohol concentration in the blood measures the alcohol in the breathing air at a time determined by a time control. This time is determined by a given time interval beginning within the expiration period. The rate of flow must not drop below a determined minimum rate during this time interval and the breathing air must always flow in an expiration direction. If these two conditions are not met, an error detector determines and indicates the invalidity of the measurement.

The object of the given time interval is to ensure that the test person has already exhaled the air from the oral cavity and the air pipe, and that the measuring instrument then measures the alcohol concentration of the breathing air from the alveoli of the lungs. The expiration of the given time interval is determined by the time at which a minimum breathing air volume of preferably at least 75% of the entire breathing air volume has been exhaled. An integrator can integrate the rate of flow of the breathing air during inspiration and expiration, and from there, determine the end of the time interval by the minimum breathing air volume. This device and method is independent of the physical structure of the person being tested. Thus, the method does not prevent measuring errors caused by a test person whose lungs are too large or who does not cooperate in the test. By means of deliberate flat inhalation, the test person can simulate a too low breathing capacity. The automatically established minimum breathing air volume during the test can then be practically all mixed air from the lungs, oral and pharyngeal space (See German Offenlegungschrift No. 24 28 352).

Another known method and the respective arrangement therefor are based on the consideration that the actual alcohol concentration in the breathing air can only be determined if that part of the exhaled air is analyzed for its alcohol content, which could establish equilibrium with the alcohol concentration of the blood in the alveoli of the lungs. The oscillating air from the oral and pharyngeal cavity and the mixed air must, therefore, be separated from the alveolar air in the measurement procedure. The method and the respective arrangement for this type of device resolves this problem by using an infrared measuring device which constantly measures the alcohol concentration during the sampling period. The change in time of the measured value is determined in a threshold value comparator, which represents the measurement for the rate of rise of the alcohol concentration.

A measured value is transmitted to the indicator only when the rate of rise drops below a given threshold value. This first condition results from the fact that the portion of the oscillating air from the oral and pharyngeal space diminishes with the drop of the rate of rise, and when it drops below the threshold value, only alveolar air is contained in the measuring channel of the arrangement. Another condition is that the measured value is transmitted when the rate of flow of the exhaling air is determined by a flow meter must be above a given value during a given time interval until the measured value is transmitted. This additional condition ensures the provided course of the measuring method. The alcohol concentration is measured by an infrared measuring device with a short response time connected into the breathing air current.

By meeting these three conditions, namely, determination of the change in time of the alcohol signal; measurement of the rate of exhalation compared to a given value, and minimum maintenance of this value over a given time, the device becomes voluminous and complicated and, moreover, requires corresponding supervision (See German Offenlegungschrift No. 26 10 578).

SUMMARY OF THE INVENTION

An object of the present invention is to provide a method and an arrangement for determining the alcohol concentration in the blood by measuring the alcohol concentration of the breathing air, whose measuring result is not influenced by deceptive maneuvers by the person being tested unwillingly, such as by flat breathing.

The inventive method for determining the alcohol concentration in the blood by measuring the alcohol concentration and the humidity in the breathing air makes deception by unwilling test persons or false sampling impossible, regardless of what breathing technique is used by the test person. Since the measuring result is determined by the ratio of the measured amount of alcohol and the humidity, it is independent of whether the sample was taken from the lungs or from other air passages. It is also irrelevant for the measuring result whether the sample volume originates from one or several breaths.

The solution of the problem embodied by the apparatus of the invention is preferably achieved in a simple manner by using known structural elements. This ensures a reliable performance of the alcohol tests and complicated aggravating checks on the part of the tester are unnecessary.

Accordingly, another object of the present invention is to provide a method of determining the alcohol concentration in the blood of a person by testing a person's breath, comprising, maintaining at least a minimum flow rate of the person's breath to form a test sample of breath, measuring the alcohol amount in the test sample, measuring an increase in humidity in the test sample over an ambient humidity in the air, and determining the ratio between the alcohol amount and the increase in humidity to obtain a value which is proportional to the alcohol concentration in the blood of the person.

A further object of the present invention is to provide an apparatus for detecting the alcohol concentration in the blood of a person by testing the person's breath, comprising, a breathing tube for receiving a flow of the person's breath, alcohol and water-sensing means connected to said breathing tube for sensing an amount of alcohol in the breath in the breathing tube and an increase in humidity in the breath in the breathing tube over an ambient humidity in the air, and circuit means connected to said alcohol and water-sensing means for forming the ratio between the amount of alcohol and the increase in humidity which is proportional to the alcohol concentration in the blood of the person.

A still further object of the invention is to provide an apparatus for determining the alcohol concentration in the blood of a person by testing the person's breath which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic representation of the inventive device for determining the alcohol concentration in the blood of a person by testing the person's breath which also illustrates the method of the invention.

DESCRIPTION OF THE PREFERRED EMBODIMENT

Referring to the drawing in particular, the invention embodied therein, comprises, a method and apparatus for determining the alcohol concentration in the blood of a person by testing the person's breath and, specifically, by measuring the amount of alcohol in the person's breath, as well as the increased humidity of the person's breath over an ambient humidity in the surrounding air and finding the ratio of the alcohol amount over the increase in humidity, which ratio is proportional to the alcohol concentration in the person's blood.

In accordance with the invention, the test person 44 exhales through breathing tube 1. The tube 1 is heated in order to prevent condensation by means 42, for example. For sanitary reasons, the tube can be equipped with a replaceable mouthpiece.

Breathing tube 1 is equipped with an alcohol water sensor or sensing means 3. In the embodiment shown, the sensor means comprises an optical sensor. The alcohol is measured as an optical absorption at 3.4 $\mu$m wavelength, and the water at 2.7 $\mu$m wavelength. The two wavelengths are passed alternately through a filter 16 for alcohol, and a filter 17 for water installed in a filter wheel 15 which is rotated by a drive 40. A lamp 10 illuminates measuring space 14 in breathing tube 1 over a condenser or lens 11 and through windows 12 and 13. A detector 18 is arranged over one end of filter wheel 15, and generates signals corresponding to the position of filter wheel 15, namely, a signal S/S is formed over line 19. There is a signal at S, and at zero, the optical path between filters 16 and 17 is blocked. A signal A/W is formed over line 20, whereby, an alcohol signal appears at A over a line 24 and a water signal appears at zero.

A detector 21 is provided at another end of wheel 15, which transforms the light from measuring space 14 into an electrical signal. After amplification and scaling in preamplifier 22, it is fed to an analog-digital converter 23. The output of ADC 23 is connected to two gates 25 and 26 which, if their switching conditions are met, store the value on line 24 in memories 27 for alcohol and 28 for water. A memory 29 contains the alcohol zero value and a memory 30 contains the water content of the ambient air value.

A subtractor 31 subtracts the alcohol zero value of memory 29 from the alcohol value of memory 27. Thus, at its output, we have;

$Ra$ = alcohol concentration (mg·l$^{-1}$)

in the sample volume of breath in space 14.

A subtractor 32 subtracts from the stored value of $Rwa$ = water concentration (mg·l$^{-1}$)

in the sample volume of memory 28, the stored value of $Rwl$ = water concentration (mg·l$^{-1}$)

of the atmosphere of memory 30.

The value $Rwa-Rwl$ thus appears at its output.

Principally, it would suffice to divide the value at the output of subtractor 31 by the value at the output of subtractor 32 and to multiply the quotient by a suitable constant in order to obtain the alcohol reading. The indicated value comprises the tiny amount of breathing air that is contained in measuring space 14. The reading will vary correspondingly by variations within the amount of breathing air. In order to obtain a convincing value, information about a number of single measurements is required. This is also realized with this arrangement of the invention.

To this end, a flow sensor 2 operating according to the Karman vortex principle is arranged in breathing tube 1 having a flow diverter 7 and a pressure sensor 4. In the Karman vortex, both the number of vortices and their amplitude depend on the flow of breath in tube 1. By installing a signal threshold in an electronic plotter 5, the sensitivity is limited at the bottom. Plotter 5 also produces a measurement pulse in line 6. Interfering influences, which would be noticeable over pressure sensor 4, are thus eliminated. The circuit thus includes Karman vortex counter. The amount of breathing air not delivered, which appears only at low rates of flow, does not affect the result. For averaging, the output from subtractor 31 is counted in memory 33, one each per pulse on line 6, thus $$\int Ra \cdot dv.$$

The value dv is the volume of breathing air tested. In memory 34 correspondingly from the output of subtractor 32

$$\int (Rwa - Rwl) \cdot dv$$

The addition of the partial samples from the pulses is continued until a certain minimum water increase Mw is contained in memory 34.

A suitable value for this integral, based on ambient air of 25° C. and a relative humidity of 43%, and an amount of 3 liters, is a value of Mw=85 mg. In a subtractor 35, following memory 34, this fixed value is subtracted from the value from memory 34. As soon as the difference is positive, hence, the value from the sample volume is greater, line 36 receives a signal and the sampling is ended. To this end, additional pulses over line 6 are blocked and the amount of alcohol in the breathing air, and thus in the blood, is determined in computer 37 from the ratio of the measured amount of alcohol Ra and the measured water increase Rwa−Rwl:

$$Ra/(Rwa-Rwl)$$

An indicator 38 which can also be designed as a printer, indicates the result. Breathing tube 1 is equipped at the output with a relief valve 42 with which measuring errors caused by the possible inflow of ambient air are prevented. Prior to the measurement, breathing tube 1 is flushed with ambient air by an air conveyor or blower 41 over air line 40, at the same time a signal appears on reset line 39. The output values are thus stored in memories 29 and 30, and memories 33 and 34 are set back to zero.

While a specific embodiment of the invention has been shown and described in detail to illustrate the application of the principles of the invention, it will be understood that the invention may be embodied otherwise without departing from such principles.

What is claimed is:

1. A method of determining the alcohol concentration in the blood of a person by testing a person's breath, comprising, maintaining at least a minimum flow rate for the person's breath, measuring the alcohol amount in the test sample, measuring an increase in humidity in the test sample over an ambient humidity in the air, and determining the ratio between the alcohol amount and the increase in humidity to obtain a value which is proportional to the alcohol concentration in the blood of the person.

2. A method, as claimed in claim 1, wherein said measuring of the alcohol amount comprises passing light through the test sample, filtering the light for producing a characteristic absorption for the alcohol and detecting the filtered light to indicate the alcohol amount.

3. A method, as claimed in claim 1, wherein said measuring of an increase in humidity comprises passing light through the test sample, filtering the light to produce a characteristic absorption for water and detecting the filtered light to determine the increase in humidity.

4. A method, as claimed in claim 1, comprising, measuring the alcohol amount and the increase in humidity a plurality of times for a plurality of test samples and averaging the results to form an average alcohol amount and average increase in humidity.

5. A method, as claimed in claim 4, further including measuring the minimum flow rate of the person and measuring the alcohol amount and increase in humidity only when said flow rate is above a selected minimum value.

6. An apparatus for determining the alcohol concentration in the blood of a person by testing the person's breath, comprising, a breathing tube for receiving a flow of the person's breath, alcohol and water-sensing means connected to said breathing tube for sensing an amount of alcohol in the breath and an increase in humidity in the breath over an ambient humidity in the air, and circuit means connected to said alcohol and water-sensing means for producing the ratio between the amount of alcohol and the increase in humidity which is proportional to the alcohol concentration in the blood of the person.

7. An apparatus, as claimed in claim 6, wherein said alcohol and water-sensing means comprises a movably mounted filter wheel carrying an alcohol light filter for passing a wavelength of light for determining the optical absorption of alcohol and a water light filter for passing a wavelength of light for determining the optical absorption of water, said filter wheel mounted on one side of said breathing tube and a light mounted on an opposite side of said breathing tube for passing light through the breathing tube and through the test sample and drive means for moving said filter wheel for illuminating one of said alcohol and water light filters at a time.

8. An apparatus, as claimed in claim 7, further including filter wheel position detector means connected to said breathing tube for sensing the position of said filter wheel to indicate which of said alcohol and water light filters is illuminated by said light.

9. An apparatus, as claimed in claim 6, further including flow sensor means in said breathing tube for sensing a flow of breath in said breathing tube connected to said circuit means for activating said circuit means to form the ratio between the alcohol amount and the increasing humidity amount only when the flow of breath in said breathing tube is above a selected minimum value.

10. An apparatus, as claimed in claim 9, wherein said flow sensor means comprises a whirl rod disposed in said breathing tube and across the flow path of the person's breath therein and a pressure sensor downstream of said whirl rod for sensing the pressure produced by a whirl of breath in the breath flow path, said circuit means including a Karman vortex counter for sensing the flow of breath in the breathing tube.

11. An apparatus, as claimed in claim 6, further including a relief valve in said breathing tube downstream of said sensing means for opening to permit the breath to pass out of said breathing tube and closing to prevent outside air from entering said breathing tube.

12. An apparatus, as claimed in claim 6, further including a blower connected to said breathing tube for flushing air and breath out of said breathing tube.

13. An apparatus, as claimed in claim 6, wherein said circuit means comprises means for receiving the sensed amount of alcohol and sensed amount in increase in humidity a plurality of times and for averaging said sensed amounts and determining the ratio therebetween.

* * * * *